United States Patent
Stutz et al.

(10) Patent No.: US 6,730,798 B2
(45) Date of Patent: May 4, 2004

(54) PROCESS FOR THE PREPARATION OF SUBSTITUTED OCTANOYL AMIDES

(75) Inventors: Stefan Stutz, Basel (CH); Peter Herold, Basel (CH); Felix Spindler, Starrkirch-Wil (CH)

(73) Assignee: Speedel Pharma AG, Basel (CH)

( * ) Notice: Subject to any disclaimer, the term of this patent is extended or adjusted under 35 U.S.C. 154(b) by 15 days.

(21) Appl. No.: 10/312,987

(22) PCT Filed: Jun. 26, 2001

(86) PCT No.: PCT/CH01/00399

§ 371 (c)(1),
(2), (4) Date: Jan. 3, 2003

(87) PCT Pub. No.: WO02/02508

PCT Pub. Date: Jan. 10, 2002

(65) Prior Publication Data

US 2003/0149303 A1 Aug. 7, 2003

(51) Int. Cl.$^7$ .............................. C07D 305/12
(52) U.S. Cl. ................. 549/323; 549/561; 562/471; 562/495; 564/191; 560/104
(58) Field of Search ................. 549/323, 561; 564/191; 562/471, 495; 560/104

(56) References Cited

FOREIGN PATENT DOCUMENTS

| EP | 0 678 500 A | 10/1995 |
|----|-------------|---------|
| EP | 0 678 503 A | 10/1995 |
| EP | 0 678 514 A | 10/1995 |
| WO | 01 09079 A  | 2/2001  |
| WO | 01 09083 A  | 2/2001  |

OTHER PUBLICATIONS

Peter Herold et al: "A Versatile and Stereocontrolled Synthesis of Hydroxyethylene Dipeptide Isosters" *Journal of Organic Chemistry*, American Chemical Society. Easton, U.S., vol. 54, No. 5, Mar. 3, 1989, pp. 1178–1185, XP002149098.

Goschke R. et al: "Design and Synthesis of Novel 2,7–dialkyl Substituted 5(S)–amino–4(S)–hydroxy–8–phenyl–octanecarboxamides as In Vitro Potent Peptidomimetic Inhibitors of Human Renin" *Bioorganic & Medicinal Chemistry Letters*, Oxford, GB, vol. 7, No. 21, Nov. 4, 1997, pp. 2735–2740, XP004136522.

Rueger H. et al: "A Convergent Synthesis Approach Towards CGP60536B, A Non–peptide Orally Potent Renin Inhibitor, Via an Enantiomerically Pure Ketolactone Intermediate" *Tetrahedron Letters*, Elsevier Science Publishers, Amsterdam, NL, vol. 41, No. 51, Dec. 16, 2000, pp. 10085–10089, XP004225222.

Sandham D. A. et al: "A Convergent Synthesis of the Renin Inhibitor CGP60536B" *Tetrahedron Letters*, Elsevier Science Publishers, Amsterdam, NL, vol. 41, No. 51, Dec. 16, 2000, pp. 10091–10094, XP004225223.

*Primary Examiner*—Amelia Owens
(74) *Attorney, Agent, or Firm*—Wenderoth, Lind & Ponack, L.L.P.

(57) ABSTRACT

Compounds of formula (II) are simultaneously halogenated in the 5 position and hydroxylated in the 4 position under lactonization, the halolactone is converted into a hydroxylactone and then the hydroxy group into a leaving group, the leaving group is replaced with azide, the lactone amidated and then the azide converted to the amine group, in order to obtain compounds of formula (I).

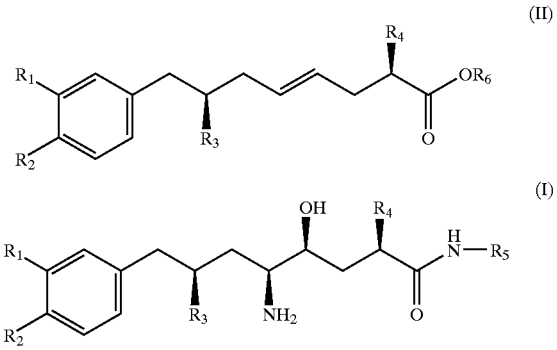

10 Claims, No Drawings

PROCESS FOR THE PREPARATION OF SUBSTITUTED OCTANOYL AMIDES

The invention relates to a process for the preparation of 2(S),4(S),5(S), 7(S)-2,7-dialkyl-4-hydroxy-5-amino-8-aryl-octanoyl amides and their physiologically acceptable salts; and the new compounds used as intermediates in the multistage process.

In EP-A-0 678 503, δ-amino-γ-hydroxy-ω-aryl-alkanecarbox-amides are described, which exhibit renin-inhibiting properties and could be used as antihypertensive agents in pharmaceutical preparations. The manufacturing procedures described are unsatisfactory in terms of the number of process steps and yields and are not suitable for an industrial process. A disadvantage of these processes is also that the total yields of pure diastereomers that are obtainable are too small.

It has now been surprisingly found that these alkane-carboxamides can be prepared both in high total yields and in a high degree of purity, and that selectively pure diastereomers are obtainable, if the double bond of 2,7-dialkyl-8-aryl-4-octenic acid or 2,7-dialkyl-8-aryl-4-octenic acid ester is simultaneously halogenated in the 5 position and hydroxylated in the 4 position under lactonization, the halolactone is converted to a hydroxylactone and then the hydroxy group is converted to a leaving group, the leaving group substituted with azide, the lactone amidated and then the azide converted to the amine group. Apart from the high yields and stereoselectivities in the individual process steps, particular attention is drawn to the fact that substantially fewer by-products are formed in the azidation step.

A primary object of the invention is a process for the preparation of compounds of formula I,

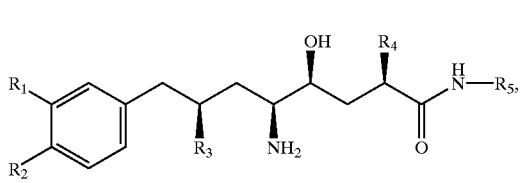

(I)

wherein
$R_1$ and $R_2$ are, independently of one another, H, $C_1$–$C_6$alkyl, $C_1$–$C_6$halogenalkyl, $C_1$–$C_6$alkoxy, $C_1$–$C_6$alkoxy-$C_1$–$C_6$alkyl, or $C_1$–$C_6$alkoxy-$C_1$–$C_6$alkyloxy, $R_3$ is $C_1$–$C_6$alkyl, $R_4$ is $C_1$–$C_6$alkyl, and $R_5$ is $C_1$–$C_6$alkyl, $C_1$–$C_6$hydroxyalkyl, $C_1$–$C_6$alkoxy-$C_1$–$C_6$-alkyl, $C_1$–$C_6$alkanoyloxy-$C_1$–$C_6$alkyl, $C_1$–$C_6$aminoalkyl, $C_1$–$C_6$alkylamino-$C_1$–$C_6$-alkyl, $C_1$–$C_6$-dialkylamino-$C_1$–$C_6$-alkyl, $C_1$–$C_6$-alkanoylamido-$C_1$–$C_6$-alkyl, HO(O)C—$C_1$–$C_6$-alkyl, $C_1$–$C_6$alkyl-O—(O)C—$C_1$–$C_6$alkyl, $H_2N$—C(O)—$C_1$–$C_6$alkyl, $C_1$–$C_6$alkyl-HN—C(O)—$C_1$–$C_6$alkyl or $(C_1$–$C_6$alkyl$)_2$N—C(O)—$C_1$–$C_6$-alkyl, comprising a) the reaction of a compound of formula II,

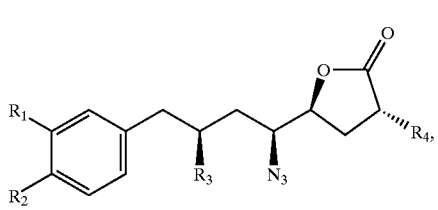

(II)

with an amine of formula $R_5$—$NH_2$ to form a compound of formula III,

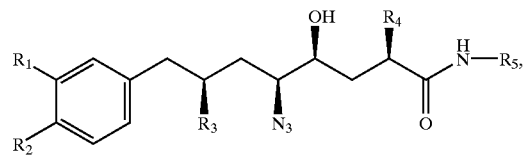

(III)

and b) reduction of the azide group of the compound of formula III to the amine group and isolation of the compounds of formula I, if necessary with the addition of a salt-forming acid, comprising the preparation of compounds of formula II by reacting c1) a compound of formula IV,

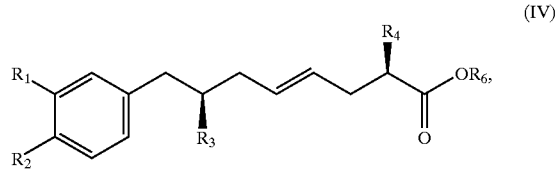

(IV)

wherein $R_6$ is $C_1$–$C_{20}$alkyl, $C_3$–$C_{12}$cycloalkyl, $C_3$–$C_{12}$cycloalkyl-$C_1$–$C_6$alkyl, $C_6$–$C_{10}$aryl or $C_6$–$C_{10}$-aryl-$C_1$–$C_6$alkyl, with a halogenation agent to form a compound of formula VI, or c2) a carboxylic acid of formula V, or a salt of this carboxylic acid,

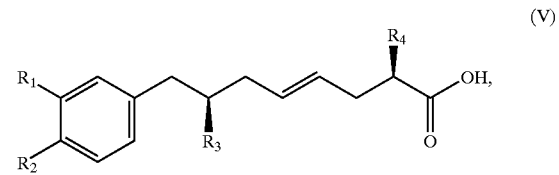

(V)

with a halogenation agent to form a compound of formula VI,

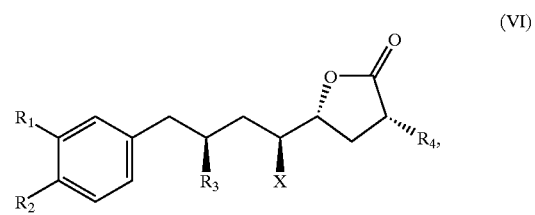

(VI)

wherein X is Cl, Br or I, d) reaction of the compound of formula VI in the presence of an alkali metal or alkaline earth metal hydroxide or an alcohol to form a compound of formula VII,

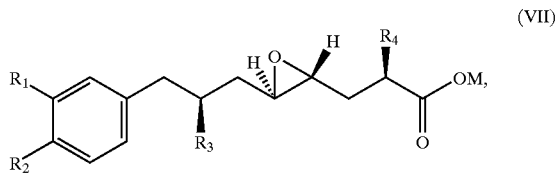

(VII)

wherein M is an alkali metal, an equivalent alkaline earth metal or the residue of an alcohol minus a hydroxyl group, e) hydrolysis of the compound of formula VII in the presence of an acid to form a compound of formula VIII,

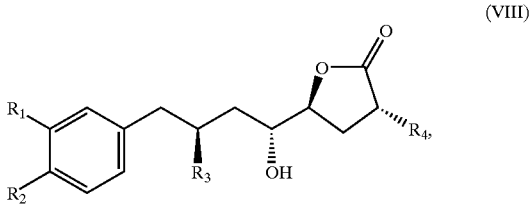

(VIII)

f) substitution of the hydrogen atom of the hydroxyl group in the compound of formula VIII and conversion thereof to a leaving group AO to form compounds of formula IX,

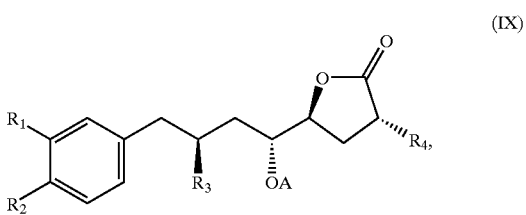

(IX)

g) and then reaction of the compound of formula IX with an azidation agent to form a compound of formula II, or h) reaction if the compound of formula VIII directly with a zinc azide/-bis-pyridine complex in the presence of a tertiary phosphine and an azodicarboxylate, if necessary in an organic solvent, to form a compound of formula II.

As an alkyl, $R_1$ and $R_2$ may be linear or branched and preferably comprise 1 to 4 C atoms. Examples are methyl, ethyl, n- and i-propyl, n-, i- and t-butyl, pentyl and hexyl.

As a halogenalkyl, $R_1$ and $R_2$ may be linear or branched and preferably comprise 1 to 4 C atoms, especially 1 or 2 C atoms. Examples are fluoromethyl, difluoromethyl, trifluoromethyl, chloromethyl, dichloromethyl, trichloromethyl, 2-chloroethyl and 2,2,2-trifluoroethyl.

As an alkoxy, $R_1$ and $R_2$ may be linear or branched and preferably comprise 1 to 4 C atoms. Examples are methoxy, ethoxy, n- and i-propyloxy, n-, i- and t-butyloxy, pentyloxy and hexyloxy.

As an alkoxyalkyl, $R_1$ and $R_2$ may be linear or branched. The alkoxy group preferably comprises 1 to 4 and especially 1 or 2 C atoms, and the alkyl group preferably comprises 1 to 4 C atoms. Examples are methoxymethyl, 1-methoxyeth-2-yl, 1-methoxyprop-3-yl, 1-methoxybut-4-yl, methoxypentyl, methoxyhexyl, ethoxymethyl, 1-ethoxyeth-2-yl, 1-ethoxyprop-3-yl, 1-ethoxybut-4-yl, ethoxypentyl, ethoxyhexyl, propyloxymethyl, butyloxymethyl, 1-propyloxyeth-2-yl and 1-butyloxyeth-2-yl.

As a $C_1$–$C_6$alkoxy-$C_1$–$C_6$alkyloxy, $R_1$ and $R_2$ may be linear or branched. The alkoxy group preferably comprises 1 to 4 and especially 1 or 2 C atoms, and the alkyoxy group preferably comprises 1 to 4 C atoms. Examples are methoxymethyloxy, 1-methoxyeth-2-yloxy, 1-methoxyprop-3-yloxy, 1-methoxybut-4-yloxy, methoxypentyloxy, methoxyhexyloxy, ethoxymethyloxy, 1-ethoxyeth-2-yloxy, 1-ethoxyprop-3-yloxy, 1-ethoxybut-4-yloxy, ethoxypentyloxy, ethoxyhexyloxy, propyloxymethyloxy, butyloxymethyloxy, 1-propyloxyeth-2-yloxy and 1-butyloxyeth-2-yloxy.

In a preferred embodiment, $R_1$ is methoxy- or ethoxy-$C_1$–$C_4$alkyloxy, and $R_2$ is preferably methoxy or ethoxy. Particularly preferred are compounds of formula I, wherein $R_1$ is 1-methoxyprop-3-yloxy and $R_2$ is methoxy.

As an alkyl, $R_3$ and $R_4$ may be linear or branched and preferably comprise 1 to 4 C atoms. Examples are methyl, ethyl, n- and i-propyl, n-, i- and t-butyl, pentyl and hexyl. In a preferred embodiment, $R_3$ and $R_4$ in compounds of formula I are in each case isopropyl.

As an alkyl, $R_5$ may be linear or branched in the form of alkyl and preferably comprise 1 to 4 C atoms. Examples of alkyl are listed hereinabove. Methyl, ethyl, n- and i-propyl, n-, i- and t-butyl are preferred.

As a $C_1$–$C_6$hydroxyalkyl, $R_5$ may be linear or branched and preferably comprise 2 to 6 C atoms. Some examples are 2-hydroxyethy-1-yl, 2-hydroxyprop-1-yl, 3-hydroxyprop-1-yl, 2-, 3- or 4-hydroxybut-1-yl, hydroxypentyl and hydroxyhexyl.

As a $C_1$–$C_6$alkoxy-$C_1$–$C_6$alkyl, $R_5$ may be linear or branched. The alkoxy group preferably comprises 1 to 4 C atoms and the alkyl group preferably 2 to 4 C atoms. Some examples are 2-methoxyethy-1-yl, 2-methoxyprop-1-yl, 3-methoxyprop-1-yl, 2-, 3- or 4-methoxybut-1-yl, 2-ethoxyethy-1-yl, 2-ethoxyprop-1-yl, 3-ethoxyprop-1-yl, and 2-, 3- or 4-ethoxybut-1-yl.

As a $C_1$–$C_6$alkanoyloxy-$C_1$–$C_6$alkyl, $R_5$ may be linear or branched. The alkanoyloxy group preferably comprises 1 to 4 C atoms and the alkyl group preferably 2 to 4 C atoms. Some examples are formyloxymethyl, formyloxyethyl, acetyloxy-ethyl, propionyloxyethyl and butyroyloxyethyl.

As a $C_1$–$C_6$aminoalkyl, $R_5$ may be linear or branched and preferably comprise 2 to 4 C atoms. Some examples are 2-aminoethyl, 2- or 3-aminoprop-1-yl and 2-, 3- or 4-aminobut-1-yl.

As $C_1$–$C_6$alkylamino-$C_1$–$C_6$alkyl and $C_1$–$C_6$dialkylamino-$C_1$–$C_6$-alkyl, $R_5$ may be linear or branched. The alkylamino group preferably comprises $C_1$–$C_4$alkyl groups and the alkyl group preferably 2 to 4 C atoms. Some examples are 2-methylaminoeth-1-yl, 2-dimethylaminoeth-1-yl, 2-ethylaminoeth-1-yl, 2-ethylaminoeth-1-yl, 3-methylaminoprop-1-yl, 3-dimethylaminoprop-1-yl, 4-methylaminobut-1-yl and 4-dimethylaminobut-1-yl.

As a $C_1$–$C_6$alkanoylamido-$C_1$–$C_6$alkyl, $R_5$ may be linear or branched. The alkanoyl group preferably comprises 1 to 4 C atoms and the alkyl group preferably 1 to 4 C atoms. Some examples are 2-formamidoeth-1-yl, 2-acetamidoeth-1-yl, 3-propionylamidoeth-1-yl and 4-butyroylamidoeth-1-yl.

As a HO(O)C—$C_1$–$C_6$alkyl, $R_5$ may be linear or branched and the alkyl group preferably comprises 2 to 4 C atoms. Some examples are carboxymethyl, carboxyethyl, carboxypropyl and carboxybutyl.

As a $C_1$–$C_6$alkyl-O—(O)C—$C_1$–$C_6$alkyl, $R_5$ may be linear or branched, and the alkyl groups preferably comprise independently of one another 1 to 4 C atoms. Some examples are methoxycarbonylmethyl, 2-methoxycarbonyleth-1-yl, 3-methoxycarbonylprop-1-yl, 4-methoxycarbonylbut-1-yl, ethoxycarbonylmethyl, 2-ethoxycarbonyleth-1-yl, 3-ethoxycarbonyl-prop-1-yl, and 4-ethoxycarbonylbut-1-yl.

As a $H_2N$—C(O)—$C_1$–$C_6$alkyl, $R_5$ may be linear or branched, and the alkyl group preferably comprises 2 to 6 C atoms. Some examples are carbamidomethyl, 2-carbamidoeth-1-yl, 2-carbamido-2,2-dimethyleth-1-yl, 2- or 3-carbamidoprop-1-yl, 2-, 3- or 4-carbamidobut-1-yl, 3-carbamido-2-methylprop-1-yl, 3-carbamido-1,2-dimethylprop-1-yl, 3-carbamido-3-ethylprop-1-yl, 3-carbamido-2,2-dimethylprop-1-yl, 2-, 3-, 4- or 5-carbamidopent-1-yl, 4-carbamido-3,3- or -2,2-dimethylbut-1-yl.

As a $C_1$–$C_6$alkyl-HN—C(O)—$C_1$–$C_6$-alkyl or ($C_1$–$C_6$alkyl)$_2$N—C(O)—$C_1$–$C_6$alkyl, $R_5$ may be linear or branched, and the NH-alkyl group preferably comprises 1 to 4 C atoms and the alkyl group preferably 2 to 6 C atoms. Examples are the carbamidoalkyl groups defined hereinabove, whose N atom is substituted, with one or two methyl, ethyl, propyl or butyl.

A preferred subgroup of compounds of formula I is that in which $R_1$ is $C_1$–$C_4$alkoxy or $C_1$–$C_4$alkoxy-$C_1$–$C_4$alkyloxy, $R_2$ is $C_1$–$C_4$alkoxy, $R_3$ is $C_1$–$C_4$alkyl, $R_4$ is $C_1$–$C_4$alkyl and $R_5$ is $H_2NC(O)$—$C_1$–$C_6$alkyl which if necessary is N-monosubstituted or N-di-$C_1$–$C_4$alkyl substituted.

A more preferred subgroup of compounds of formula I is that in which $R_1$ is methoxy-$C_2$–$C_4$-alkyloxy, $R_2$ is methoxy or ethoxy, $R_3$ is $C_2$–$C_4$alkyl, $R_4$ is $C_2$–$C_4$alkyl and $R_5$ is $H_2NC(O)$—$C_1$–$C_6$alkyl.

An especially preferred compound of formula I is that in which $R_1$ is 3-methoxy-prop-3-yloxy, $R_2$ is methoxy, $R_3$ and $R_4$ are 1-methyleth-1-yl, and $R_5$ is $H_2NC(O)$—[$C(CH_3)_2$]—$CH_2$—.

As an alkyl, $R_6$ may be linear or branched and comprise preferably 1 to 12 C atoms, 1 to 8 C atoms being especially preferred. $R_6$ is particularly preferred as a linear $C_1$–$C_4$alkyl. Some examples are methyl, ethyl and the isomers of propyl, butyl, pentyl, hexyl, heptyl, octyl, nonyl, decyl, undecyl, dodecyl, tetradecyl, hexadecyl, octacyl and eicosyl. Especially preferred are methyl and ethyl.

As a cycloalkyl, $R_6$ may preferably comprise 4 to 8 ring-carbon atoms, 5 or 6 being especially preferred. Some examples are cyclopropyl, cyclobutyl, cyclopentyl, cyclohexyl, cyclooctyl and cyclododecyl.

As a cycloalkyl-alkyl, $R_6$ may comprise preferably 4 to 8 ring-carbon atoms, 5 or 6 being especially preferred, and preferably 1 to 4 C atoms in the alkyl group, 1 or 2 C atoms being especially preferred. Some examples are cyclopropyl methyl, cyclobutyl methyl, cyclopentyl methyl or cyclopentyl ethyl, and cyclohexyl methyl or cyclohexyl ethyl.

As an aryl, $R_6$ is preferably phenyl or naphthyl.

As an aralkyl, $R_6$ is preferably benzyl or phenyl ethyl.

In formula VII, M may be an alkaline earth metal, for example Mg, Ca or Sr. Equivalent in the context of the invention means the charge equalization of cation and anion. M is preferably an alkali metal, for example Li, Na or K. Particular preference is for M as Li. If M is the residue of an alcohol minus a hydroxyl group, it may be the $R_6$ group, including the embodiments and preferences described hereinbefore, in particular alkyl and cycloalkyl.

Residue A in the leaving group AO is preferably the residue of an organic acid, for example $C_1$–$C_8$acyl, particular preference being for $C_1$–$C_8$sulfonyl. The acyl residue may be a carboxylic acid, such as formic acid, acetic acid, propionic acid, butyric acid and benzoic acid substituted if necessary with $C_1$–$C_4$alkyl, $C_1$–$C_4$alkoxy or halogen. The sulfonyl residue A may correspond for example to formula $R_7$—$SO_2$—, wherein $R_7$ is $C_1$–$C_8$alkyl, $C_1$–$C_8$halogenalkyl, $C_3$–$C_8$cycloalkyl, or phenyl or benzyl either unsubstituted or substituted with $C_1$–$C_4$alkyl, $C_1$–$C_4$alkoxy, $C_1$–$C_4$hakogenalkyl or halogen. Some examples of sulfonyl residues are methyl, ethyl, phenyl, methylphenyl, dimethyl phenyl, trimethyl phenyl, trifluoromethyl phenyl, chlorophenyl, dichlorophenyl, bromophenyl, dibromophenyl and trifluoromethyl sulfonyl.

The individual process steps may be carried out in the presence of solvent. Suitable solvents are water and organic solvents, especially polar organic solvents, which can also be used as mixtures of at least two solvents. Examples of solvents are hydrocarbons (petroleum ether, pentane, hexane, cyclohexane, methylcyclohexane, benzene, toluene, xylene), halogenated hydrocarbon (dichloromethane, chloroform, tetrachloroethane, chlorobenzene); ether (diethyl ether, dibutyl ether, tetrahydrofuran, dioxane, ethylene glycol dimethyl or diethyl ether); carbonic esters and lactones (methyl acetate, ethyl acetate, methyl propionate, valerolactone); N,N-substituted carboxamides and lactams (dimethylformamide, dimethylacetamide, N-methylpyrrolidone); ketones (acetone, methylisobutylketone, cyclohexanone); sulfoxides and sulfones (dimethylsulfoxide, dimethylsulfone, tetramethylene sulfone); alcohols (methanol, ethanol, n- or i-propanol, n-, i- or t-butanol, pentanol, hexanol, cyclohexanol, cyclohexanediol, hydroxymethyl or dihydroxymethyl cyclohexane, benzyl alcohol, ethylene glycol, diethylene glycol, propanediol, butanediol, ethylene glycol monomethyl or monoethyl ether, and diethylene glycol monomethyl or monoethyl ether; nitriles (acetonitrile, propionitrile); tertiary amines (trimethylamine, triethylamine, tripropylamine and tributylamine, pyridine, N-methylpyrrolidine, N-methylpiperazine, N-methylmorpholine) and organic acids (acetic acid, formic acid).

Process Step a)

The reaction of compounds of formula II to form compounds of formula III with a compound $R_5NH_2$ by opening of the lactone ring can be carried out with or without solvent. The reaction is expediently carried out in the presence of alcohols or amines, which can form activated carbonic esters or carboxamides. Such compounds are well-known. These may be 2-hydroxypyridine, N-hydroxycarboxamides and imides, and carboximides (N-hydroxysuccinimide). Organic solvents are used as solvent, tertiary amines being of advantage, for example trimethylamine or triethylamine. The reaction temperature may range for example from approximately 40° C. to 150° C. and preferably from 50° C. to 120° C.

Process Step b)

Reduction of the azide group to the amine group in the compounds of formula III takes place in a manner known per se (see Chemical Reviews, Vol. 88 (1988), pages 298 to 317), for example using metal hydrides or more expediently using a catalytic method with hydrogen in the presence of homogeneous (Wilkinson catalyst) or heterogeneous catalysts, for example Raney nickel or precious metal catalysts such as platinum or palladium, if necessary on substrates such as carbon. The hydrogenation can also be carried out if necessary catalytically under phase transfer conditions, for example with ammonium formate as hydrogen donor. It is of advantage to use organic solvents. The reaction temperature may range for example from approximately 0° C. to 200° C. and preferably from 10° C. to 100° C. Hydrogenation may be carried out at normal pressure or increased pressure up to 100 bar, for example, and preferably up to 50 bar.

The compounds of formula I may be converted to addition salts in a manner known per se by treatment with monobasic or polybasic, inorganic or organic acids. Hemifumarates are preferred.

Process Step c1)

Suitable chlorination, bromination and iodination agents are elemental bromine and iodine, in particular N-chlorine, N-bromine and N-iodocarboxamides and dicarboximides. Preferred are N-chloro, N-bromo and N-iodophthalimide and especially chloro, N-bromo and N-iodosuccinimide, as well as tertiary butyl hypochlorite and N-halogenated sulfonamides and sulfonimides, for example chloramine T. The reaction is advantageously carried out in organic solvents miscible with water, such as tetrahydrofuran or dioxane in the presence of at least an equivalent volume of water. The reaction takes place first at low temperatures, for example −20 to 10° C., and then at elevated temperatures, for example 30 to 100° C. The presence of inorganic or organic acids may be advantageous. Suitable acids are for example formic acid, acetic acid, methanesulfonic acid, trifluoroacetic acid, trifluoromethanesulfonic acid, toluenesulfonic acid, $H_2SO_4$, $H_3PO_4$, hydrogen halides, acid ion exchange resins, and acids immobilized on solid carriers. The halolactone may be isolated for example by extraction with organic solvents.

Process Step c2)

Suitable chlorination, bromination and iodination agents are elemental bromine and iodine, in particular N-chloro, N-bromo and N-iodocarboxamides and dicarboximides. Preferred are N-chloro, N-bromo and N-iodophthalimide and especially chloro, N-bromo and N-iodosuccinimide, as well as tertiary butyl hypochlorite and N-halogenated sulfonamides and sulfonimides, for example chloramine T. The reaction is advantageously carried out in organic solvents, such as halogenated hydrocarbons (chloroform, dichloromethane). The reaction temperature may range for example from approximately −70° C. to ambient temperature and preferably from −30° C. to 10° C. The halolactone may be isolated for example by extraction with organic solvents.

Suitable salts of carboxylic acids of formula V are for example alkali metal or alkaline earth metal salts, for example sodium, potassium, magnesium or calcium salts, as well as ammonium salts. The ammonium salts may derive from ammonia, primary, secondary or tertiary amines, or they may be quaternary ammonium salts. The amines may be acyclic or cyclic and comprise heteroatoms from the C and S group. The amines may comprise 1 to 18 C atoms, 1 to 12 being preferred and 1 to 8 especially preferred. Quaternary ammonium salts may comprise 4 to 18 C atoms, 4 to 12 being preferred and 4 to 8 especially preferred. Some examples of amines are methylamine, dimethylamine, triethylamine, ethylamine, diethylamine, triethylamine, propylamine, dipropylamine, Tripropylamine, isopropylamine, butylamine, dibutylamine, tributylamine, phenylamine, methylethylamine, methyldiethylamine, phenylmethylamine, benzylamine, cyclopentylamine, cyclohexylamine, piperidine, N-methyl-piperidine, morpholine, pyrrolidine, and 2-phenylethylamine. Salt formation allows a more efficient purification of the carboxylic acids of formula V with regard to their optical and chemical purity, especially when crystalline salts are formed with the selection of amines. The salts may be converted before the reaction to the carboxylic acids of formula V. However, the salts may also be used directly for halolactonization. In this case, the addition of acids, for example trifluoroacetic acid or other strong acids, is recommended, as described under process step c1).

The halolactonization is surprisingly stereoselective, and the desired cis-halolactones are formed in yields of up to 90% or more.

Process Step d)

The reaction of a compound of formula VI with at least equimolar quantities of alkali or alkaline earth metal hydroxides is expediently carried out in a polar organic solvent, for example alcohols such as isopropanol, and at low temperatures of, for example, −20 to 30° C. Aqueous solutions of hydroxides are preferably used, lithium hydroxide being especially preferred. The compound of formula VII does not need to be isolated, but the reaction mixture can be used directly in process step e). The desired stereoisomer is also formed in this step at high yields of up to 90% or more.

The reaction of a compound of formula VI with at least equimolar quantities of an alcohol, especially a $C_1$–$C_8$alkanol and in particular methanol or ethanol, is expediently carried out in a polar organic solvent, for example ethers or the alkanols used for esterification, and at low temperatures of, for example −20 to 30° C. Bases are preferably used as well, for example alkali metal hydrogencarbonates or alkali metal carbonates, potassium hydrogencarbonate being especially preferred. The compound of formula VII does not need to be isolated, but the reaction mixture can be used directly in process step e). The desired stereoisomer is also formed in this reaction at high yields of up to 90% or more.

Process Step e)

Lactonization of the compounds of formula VII to form compounds of formula VIII is expediently carried out at a temperature of −20 to 50° C. and in the presence of a preferably polar solvent, such as an alcohol (isopropanol) or ether (tetrahydrofuran, dioxane). It is advantageous to use inorganic acids, especially mineral acids such as hydrochloric acid, hydrobromic acid or sulfuric acid. The hydroxylactone of formula VII may be isolated for example by extraction with organic solvents. The desired stereoisomer is also formed in this step at high yields of up to 90% or more.

Process Step f)

Conversion of the hydroxy group to a leaving group may be carried out in organic solvents, preferably polar organic solvents, and at temperatures of −20 to 50° C. Acid halogenides, such as acid chlorides and acid bromides, are preferably used as reagents. Sulfonyl chlorides or bromides are especially preferred. The reaction is advantageously carried out in the presence of equivalent quantities of a base for bonding of the acid. Suitable bases are in particular tertiary amines, such as trimethylamine or triethylamine and dimethylaminopyridine. The hydroxylactone of a compound of formula VII may be isolated for example by extraction with organic solvents. The yields are up to 90% or more.

Process Step g)

Suitable azidation agents are for example metal azides, especially alkaline earth metal azides and alkali metal azides, as well as silyl azides. Especially preferred azidation agents are lithium azide, sodium azide and potassium azide. The reaction may be carried out in organic solvents, such as 1,3-dimethyl-3,4,5,6-tetrahydro-2(1H)-pyrimidinone (DMPU), dimethylacetamide (DMA), N-methylpyrrolidone (NMP), dimethylformamide (DMF), 1,3-dimethylimidazolidinone (DMI), toluene or methylcyclohexane. The reaction temperature may range for example from approximately 20° C. to 150° C. and preferably from 50° C. to 120° C. It may be expedient to include the use of phase transfer catalysts. The preparation and synthetic use of azides are described for example by E. F. V. Scriven in Chemical Reviews, Vol. 88 (1988), pages 298 to 317 The yield amounts to an outstanding 70% or more.

In one variant, the introduction of the leaving group in process step f) and the azidation in process step g) may be carried out simultaneously in one reaction vessel.

Process Step h)

In one variant, the azidation may also be carried out directly with the hydroxyl compound of formula VIII. This reaction has been described by David. L. Hughes in Organic Preparations and Procedures Int. (1996), 28 (2), pp. 127–164 and by M. C. Viaud et al. in Synthesis (1990), pp. 130 to 131. The azidation is carried out with at least equimolar quantities of zinc azide/bis-pyridine in the presence of, for example, triphenylphosphine in quantities of 2 equivalents or more, and approximately equal quantities of an azodicarboxylate such as azodiisopropylcarboxylate. The reaction is carried out in an organic solvent, especially an aromatic hydrocarbon, such as benzene, toluene or xylene. The reaction temperature may be −20 to 80° C.

Some intermediates prepared using the process according to the invention are new and represent further objects of the invention.

A further object of the invention is thus a compound of formula X,

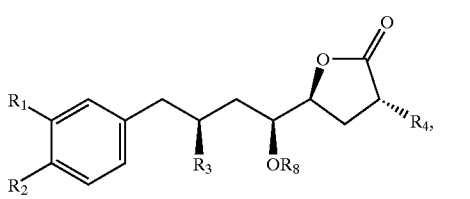

(X)

wherein
$R_1$ and $R_2$ are, independently of one another, H, $C_1$–$C_6$alkyl, $C_1$–$C_6$halogenalkyl, $C_1$–$C_6$alkoxy, $C_1$–$C_6$alkoxy-$C_1$–$C_6$alkyl, or $C_1$–$C_6$alkoxy-$C_1$–$C_6$alkyloxy, $R_3$ is $C_1$–$C_6$alkyl, $R_4$ is $C_1$–$C_6$alkyl, and $R_5$ is $C_1$–$C_6$alkyl, $C_1$–$C_6$hydroxyalkyl, $C_1$–$C_6$alkoxy-$C_1$–$C_6$-alkyl, $C_1$–$C_5$alkanoyloxy-$C_1$–$C_6$alkyl, $C_1$–$C_6$aminoalkyl, $C_1$–$C_6$alkylamino-$C_1$–$C_6$-alkyl, $C_1$–$C_6$-dialkylamino-$C_1$–$C_6$-alkyl, $C_1$–$C_6$-alkanoyl-.

An object of the invention in a broader sense is a compound of formula VII,

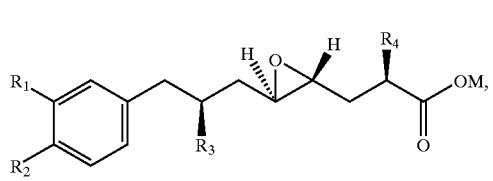

(VII)

wherein M is an alkali metal, an equivalent alkaline earth metal or the residue of an alcohol minus a hydroxyl group, and
$R_1$ and $R_2$ are, independently of one another, H, $C_1$–$C_6$alkyl, $C_1$–$C_6$halogenalkyl, $C_3$–$C_6$alkoxy, $C_1$–$C_6$alkoxy-$C_1$–$C_6$alkyl, or $C_1$–$C_6$alkoxy-$C_1$–$C_6$alkyloxy, $R_3$ is $C_1$–$C_6$alkyl, and $R_4$ is $C_1$–$C_6$alkyl.

For residues $R_1$, $R_2$, $R_3$, and $R_4$, as well as for M, in compounds of formula VII, the embodiments and preferences described hereinbefore apply.

An object of the invention is a compound of formula XIII

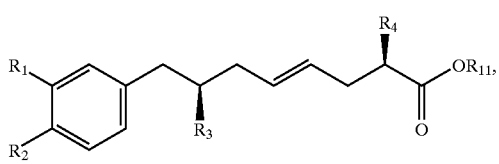

(XIII)

wherein $R_{11}$ is an alkali metal, an equivalent alkaline earth metal, hydrogen or the residue of an alcohol minus a hydroxyl group, and
$R_1$ and $R_2$ are, independently of one another, H, $C_1$–$C_6$alkyl, $C_1$–$C_6$halogenalkyl, $C_1$–$C_6$alkoxy, $C_1$–$C_6$alkoxy-$C_1$–$C_6$alkyl, or $C_1$–$C_6$alkoxy-$C_1$–$C_6$alkyloxy, $R_3$ is $C_1$–$C_6$alkyl, and $R_4$ is $C_1$–$C_6$alkyl, For residues $R_1$, $R_2$, $R_3$, $R_4$, and $R_{11}$ in compounds of formula XIII, the embodiments and preferences described hereinbefore apply.

The carboxylic acids of formula V used in process step c) may be prepared in a manner known per se by hydrolysis of hydrolysable acid derivatives such as carbonic esters, carbooxamides or carboxylates. The hydrolysis may be carried out with acids or bases. Hydrolysis with a base is preferred, for example with alkali metal hydroxides (LiOH, KOH and NaOH), which can be added as aqueous solution or as a solid. The reaction is advantageously carried out in water, organic solvents (alcohols and ethers) or mixtures thereof. The reaction temperature may range up to the boiling temperature of the solvent used. After removal of the solvent, the residue of the reaction is expediently taken up with an aqueous acid, such as hydrochloric acid, and the compound of formula V is extracted (for example with ethers) and purified. The hydrolysis is quantitative, and the pure compound of formula V is obtained in yields of more than 90%. It is possible to carry out the hydrolysis at the same time as the halolactonization in one reaction vessel. The hydrolysis may also be carried out enzymatically.

The compounds of formula XIII are obtainable by reacting a compound of formula XIV

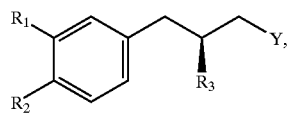

(XIV)

with a compound of formula XV,

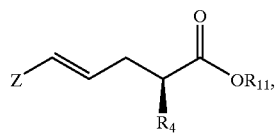

(XV)

wherein $R_1$ to $R_4$, and $R_{11}$ are as defined hereinbefore, including the preferences, Y is Cl, Br or I, and Z is Cl, Br or I, in the presence of an alkali metal or alkaline earth metal. Y and Z are preferably Br and especially Cl.

The coupling of Grignard reagents with alkenyl halogenides in an ether such as tetrahydrofuran or dioxane as solvents in the presence of catalytic quantities of a soluble metal salt or metal complex, for example an iron, nickel or palladium salt or an iron, nickel or palladium complex (such as iron trichloride, iron acetonyl acetate iron benzoyl acetonate, nickel acetonyl acetate, and iron, nickel or palladium complexes with tertiary phosphines or ditertiary diphosphines such as triphenylphosphine, tricyclohexylphosphine, 1,2-diphenylphosphinoethane, 1,2-diphenylphosphinopropane, 1,2-diphenylphosphinofuran, and 1,2-diphenylphosphinobutane is known. Examples of metal complexes and metal complex salts are dichloronickel (1,2-diphenylphosphinoethane) and dichloropalladium(1,2-diphenylphosphinoethane). The presence of an additive stabilizing the metal salts or metal complexes and metal complex salts can be of advantage. Examples are DMPU, N-methylpyrrolidone, N,N-dimethylformamide, N,N-dimethylacetamide, N-methyl-morpholine, amines such as triethylamine and tetramethylethylenediamine, as well as mixtures of at least two of these additives. When using iron acetonylacetate, the addition of a mixture of DMPU and tetramethylethylendiamine has proved successful. When using dichloronickel(1,2-diphenylphosphinoethane), the addition of triethylamine has proved to be of advantage.

The reaction is described by G. Cahiez et al. in Synthesis (1998), pp. 1199–1200. The reaction temperature may for example be −50 to 80° C., preferably −20 to 50° C. Catalytic quantities may for example be 0.1 to 20% by weight in relation to a compound of formula XIV. It is expedient to carry out the reaction so that initially a compound of formula XIV is converted to a Grignard compound (for example with magnesium) and then adding a solution of a compound of formula XV, metal salt, metal complex, or metal complex salt and the stabilizing additive, or vice versa.

It may be of advantage if only catalytic quantities of an additive stabilizing the metal complexes, for example triethylamine or DMPU, are used. Catalytic quantities may for example be 0.1 to 10 mol percent, preferably 1 to 5 mol percent, in relation to compounds of formula XIV or XV.

Compounds of formula XIV in the form of their racemates or enantiomers are known or capable of being prepared according to analogous processes. For example, $RIR_2$phenylaldehyde may be reacted with $R_3$diethoxyphosphorylacetic acid ester to form 2-$R_3$-3-($R_1R_2$phenyl)acrylic acid esters, these may then be hydrogenated to form the corresponding propionic acid esters, the ester group saponified and the carboxylic acid reduced to alcohol, and finally the hydroxyl group substituted with halogen. Enantiomers are obtainable by separating the racemates of the carboxylic acids with for example quinine or by enzymatic resolution of the racemates of the corresponding carbonic esters. Details are described in the examples. A possible asymmetric synthesis of compounds of formula XIV is described in EP-A-0 678 503.

The compounds of formula XV are obtainable by reacting for example carbonic esters or derivatives of formula $R_4CH_2COOR_{11}$ with 1,3-dihalogenpropene in the presence of strong amine bases such as alkali metal amides (Li-N(i-propyl)$_2$ or lithium hexamethyldisilazane) to form compounds of formula XV, or by preparing through derivatization in a manner known per se carboxylic acids, carboxylic acid halogenides, carboxamides and carboxylic acid salts from e.g. the carbonic esters of formula XV. The desired enantiomers can be obtained from the racemates in a manner known per se by separating the racemates, for example by crystallization from addition salts of carboxylic acids using optically active bases. It is more advantageous to separate the racemates by treating esters of formula XV with esterases.

With the choice of carbonic esters and carboxylic acids of formulae IV and V, the compounds of formula I, which per se are complex compounds, can be prepared in a convergent and simple manner, which is especially true for this enantioselective or diastereoselective synthesis. The total yield from all process steps a) to h) may amount to 40% or more, which makes industrial application feasible.

The following examples explain the invention in more detail.

A) Preparation of Compounds of Formula IV

EXAMPLE A1

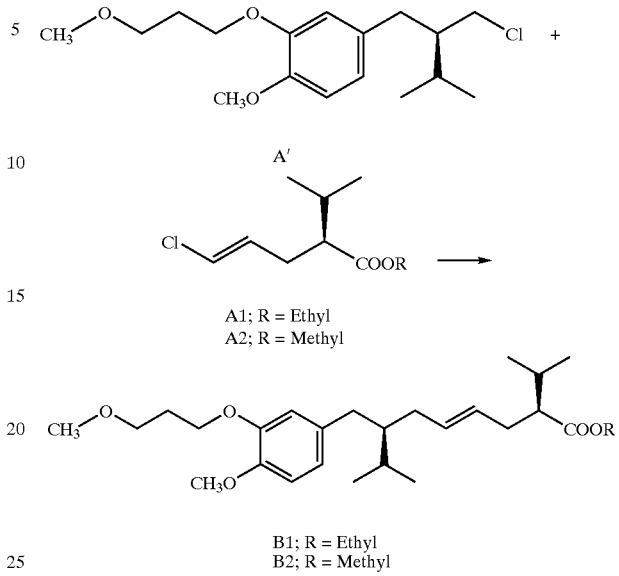

A1; R = Ethyl
A2; R = Methyl

B1; R = Ethyl
B2; R = Methyl

A mixture of 9.75 g magnesium powder and 100 ml tetrahydrofuran is heated to reflux, and 0.50 ml 1,2-dibromoethane then added over a period of 1 minute (visible exothermic reaction). A solution of 34.63 g A', 3.80 ml 1,2-dibromoethane and 300 ml tetrahydrofuran is added dropwise over a period of 30 minutes at 62–64° C. The mixture is agitated for another 30 minutes under reflux and then cooled down to ambient temperature. The reaction mixture is filtered under argon until clear and the resulting Grignard solution added dropwise over a period of 10 minutes to a solution of 20.47 g A1, 0.24 ml N-methylpyrrolidone, 0.88 g iron(III) acetylacetonate in 230 ml tetrahydrofuran at −5 to 0° C. The reaction mixture is stirred for a further 1 minute at 0° C., and 400 ml 2N hydrochloric acid is then added. The mixture is now extracted with diethyl ether (3×300 ml) and the organic phases washed consecutively with water (1×300 ml) and saturated aqueous sodium chloride solution (1×200 ml). The combined organic phases are dried over sodium sulfate, filtered and concentrated by evaporation on a Rotavapor. By means of flash chromatography (SiO$_2$ 60F; diethyl ether/hexane 1:4), title compound B1 is obtained from the residue as a slightly yellowish oil (33.8 g, 75%): TLC R$_f$=0.15 (diethyl ether-hexane 1:4). $^1$H-NMR (300 MHz, CDCl$_3$): δ 0.75–0.9 (m, 12H), 1.15 (t, 3H), 1.40 (m, 1H), 1.60 (m, 1H), 1.70–2.45 (m, 10H), 3.30 (s, 3H), 3.50 (t, 2H), 3.80 (s, 3H), 3.90–4.10 (m, 4H), 5.25 (m, 2H), 6.60 (m, 2H), 6.70 (d, 1H) ppm.

EXAMPLE A2

By analogy with example A1, the derivative is prepared by reacting A' with A2:
$^1$H-NMR (300 MHz, CDCl$_3$): δ 0.90–1.00 (m, 12H), 1.40–2.55 (m, 12H), 3.40 (s, 3H), 3.60 (t, 2H), 3.65 (s, 3H), 3.85 (s, 3H), 4.15 (t, 2H), 5.40 (m, 2H), 6.65–6.75 (m, 2H), 6.80 (d, 1H) ppm.

EXAMPLE A3

A mixture of 38.9 g magnesium powder and 400 ml tetrahydrofuran is heated to reflux, and 2.0 ml 1-bromo-2-chloroethane then added over a period of 1 minute (visible exothermic reaction). A solution of 126–0.8 g A1, 14.6 ml 1-bromo-2-chloroethane and 700 ml tetrahydrofuran is added dropwise over a period of 35 minutes at 62–64° C. The mixture is stirred for another 30 minutes under reflux and then cooled down to ambient temperature. The reaction mixture is filtered under argon until clear and the resulting Grignard solution added dropwise over a period of 20 minutes to a solution of 80.3 g A2, 5.58 ml triethylamine, and 2.11 g NidppeCl₂ in 700 ml tetrahydrofuran at 20 to 22° C. The reaction mixture is stirred for a further 1 minute at 20° C., and 1 1 1N hydrochloric acid is then added, at 15° C. Extraction is now performed with tert-butyl methyl ether (2×1 l), and the organic phases are washed consecutively with saturated aqueous sodium chloride solution/water (1:9) (2×1.2 l) and saturated aqueous sodium chloride solution (1×300 ml). The combined organic phases are dried over sodium sulfate, filtered and concentration by evaporation on a rotary evaporator. A2 which has not been converted is distilled off from the residue at 75° C. under a vacuum. Crude title compound B2 obtained in this way (171.4 g) is further reacted in example B2.

B) Preparation of Compounds of Formula V

Example B1

Preparation of Carboxylic Acid

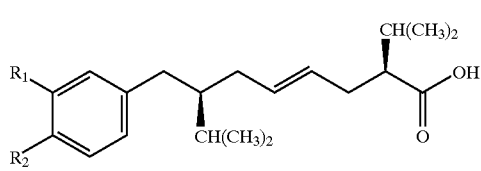
(C1)

To a solution of 22.4 g B1 and 150 ml tetrahydrofuran/ methanol/water (3:1:1) 3.6 g lithium hydroxide is added and then stirred for 48 hours under reflux. The reaction mixture is concentrated by evaporation, 500 ml 1N HCl (cold) is added to the residue, and extraction performed with tert-butyl methyl ether (3×500 ml). The organic phases are washed with saturated, aqueous NaCl solution (200 ml), dried over sodium sulfate and concentrated on a rotary evaporator. By means of flash chromatography (SiO₂ 60F/ ethyl acetate/hexane 1:1), title compound Cl is obtained from the residue as a slightly yellowish oil (19.2 g, 94%): TLC $R_f$=0.22 (diethyl ether-hexane 2:1).

¹H-NMR (300 MHz, CDCl₃): δ 0.80–1.0 (m, 12H), 1.50 (m, 1H), 1.70 (m, 1H), 1.80–2.60 (m, 10H), 3.40 (s, 3H), 3.65 (t, 2H), 3.85 (s, 3H), 4.15 (m, 2H), 5.45 (n, 2H), 6.70 (m, 2H), 6.80 (d, 1H) 7.60–9.0 (bs, 1H) ppm.

Title compound C1 can be prepared from B2 by analogy with example B1.

EXAMPLE B2

Preparation of Carboxylic Acid-Cyclohexylamine Salt

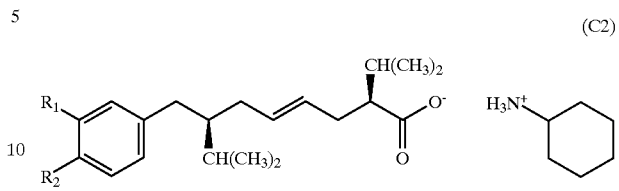
(C2)

To a solution of 171.4 g (crude) B2 and 1.07 l dioxane, 0.67 l water and 0.4 l 2N KOH are added and the mixture is then stirred under reflux for 23 hours. The reaction mixture is concentrated by evaporation, 0.6 l water is added to the residue which is washed with tert-butyl methyl ether (2×500 ml) (organic phases are discarded). The aqueous phase is acidified with 0.24 l 4N HCl and then extracted with tert-butyl methyl ether (2×0.6 l). The organic phases are washed with aqueous NaCl solution (0.6 l), dried over sodium sulfate and concentrated on a rotary evaporator. The residue is dissolved in 2 l n-hexane, 38.5 ml cyclohexylamine is added and the mixture stirred for 20 hours at room temperature. The resulting suspension is cooled to 0° C., and title compound C2 is obtained by filtration in the form of white crystals (165.6 g, 79.6%)

C) Preparation of Compounds of Formula VI

EXAMPLE C1

Preparation of

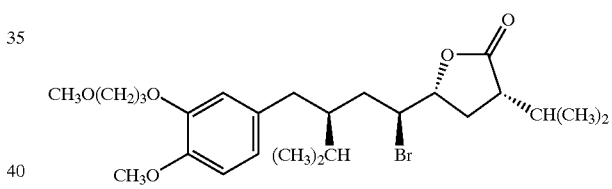
(D1)

A solution of 2.66 g C1 and 26.6 ml dichloromethane is cooled to −15° C. Then 4×0.232 g N-bromosuccinimide is added in portions every 2 minutes. The reaction mixture is stirred for another 30 minutes at −15° C. and then, over a period of 5 minutes, is introduced to 30 ml of 40% sodium hydrogen sulfite solution cooled to 0° C. The mixture is diluted with water (10 ml) and extracted with dichloromethane (2×30 ml). The organic phases are washed consecutively with water (1×30 ml) and concentrated aqueous NaCl solution (1×30 ml), then dried over sodium sulfate and concentrated on a rotary evaporator. By means of flash chromatography (SiO₂ 60F/diethyl ether/hexane 1:1) 2.98 g title compound D1 is obtained from the residue (content of title compound=approx. 89%); TLC $R_f$=0.34 (cis-lactone) and 0.38 (trans-lactone) with diethyl ether/hexane 2:1.

¹H-NMR (300 MHz, CDCl₃): δ 0.85–1.10 (m, 12H), 1.60–2.65 (m, 12H), 3.40 (s, 3H), 3.60 (t, 2H), 3.55–3.70 (m, 1H), 3.85 (s, 3H), 4.15 (t, 2H), 4.25 (m, 1H), 6.70–6.85 (m, 3H) ppm.

EXAMPLE C2

Preparation from Carbonic Ester B1 in the Presence of Water

A solution of 0.449 g B 1, 3.3 ml tetrahydrofuran and 1.7 ml water is cooled to 0° C. 0.205 g N-bromosuccinimide is added to the solution and the mixture stirred for 30 minutes at 0° C. and for 15 hours at 70° C. The reaction mixture is cooled to 0° C. and added to 30 ml of 40% aqueous sodium hydrogen sulfite solution that has been cooled to 0° C. The mixture is extracted with ethyl acetate (3×50 ml). The organic phases are washed consecutively with water (1×30 ml) and concentrated aqueous NaCl solution (1×30 ml), dried over sodium sulfate and concentrated on a rotary evaporator. By means of flash chromatography (SiO$_2$ 60F/ diethyl ether/hexane 1:1) 0.42 g title compound D1 is obtained from the residue (content of title compound= approx. 80%); TLC R$_f$=0.34 (cis-lactone) and 0.38 (trans-lactone) with diethyl ether/hexane 2:1.

$^1$H-NME (300 MHz, CDCl$_3$): δ 0.85–1.10 (m, 12H), 1.60–2.65 (m, 12H), 3.40 (s, 3H), 3.60 (t, 2H), 3.55–3.70 (m, 1H)), 3.85 (s, 3H), 4.15 (t, 2H), 4.25 (m, 1H), 6.70–6.85 (m, 3H) ppm.

EXAMPLE C3

Preparation from Cyclohexylamine Salt C2

A solution of 164.3 g C2 and dichloromethane is cooled to 0° C. 26.6 ml trifluoroacetic acid is added drop by drop and the mixture stirred for 1 hour. The reaction mixture is cooled to −20° C. Then 6×9.38 g N-bromosuccinimide is added in portions every 2 minutes. The reaction mixture is stirred for a further 2 hours at −15 to −20° C., and 160 ml 4% aqueous sodium hydrogen sulfite solution then added at 0° C. The mixture is extracted with water (1 l) and the organic phase separated off. The aqueous phase is extracted with dichloromethane (0.5 l) and the combined organic phases washed with water (1 l) and aqueous NaCl solution (0.5 l), then dried over sodium sulfate and concentrated on a rotary evaporator. The crude title compound DI obtained in this way (161.4 g) (content of title compound approx. 90%) is further reacted in examples D2 and E2.

D) Preparation of Compounds of Formula VII

EXAMPLE D1

Preparation of

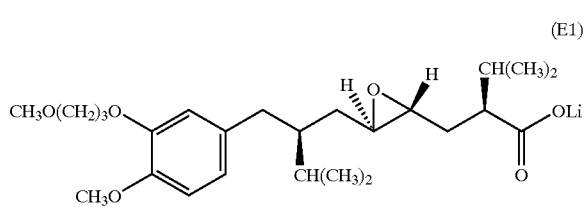

(E1)

A solution of 16.65 g D1 and 150 ml isopropanol is cooled to 0° C., then 66.6 ml 2N LiOH is added over a period of 10 minutes and the mixture stirred for 1.5 hours (the intermediate E1 is immediately reacted further in the next step).

EXAMPLE D2

Compound E1 is obtained in an analogous manner using compound D1 prepared as described under example C3 and is used in example E2.

E) Preparation of Compounds of Formula VIII

EXAMPLE E1

Preparation of

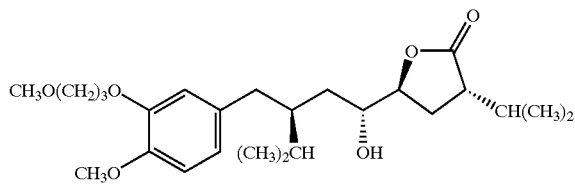

(F1)

To the reaction mixture of example D1, 100 ml 2N HCl is added drop by drop, and the reaction mixture is stirred for 1 hour at room temperature. The reaction mixture is diluted with water (500 ml) and extracted with tert-butyl methyl ether (3×250 ml). The organic phases are washed consecutively with water (2×500 ml) and concentrated aqueous NaCl solution (200 ml), dried over sodium sulfate and concentrated on a rotary evaporator. By means of flash chromatography (SiO$_2$ 60F/diethyl ether/hexane 2:1) 12.0 g title compound F1 is obtained from the residue (content of title compound=approx. 88%); TLC R$_f$=0.16 (diethyl ether/ hexane 2:1).

$^1$H-NMR (300 MHz, CDCl$_3$): δ 0.80–1.05 (m, 12H), 1.10–2.25 (m, 10H), 2.35 (m, 1H), 2.50–2.75 (m, 2H), 3.40 (s, 3H), 3.60 (t, 2H), 3.90 (s, 3H), 3.80–3.90 (m, 1H), 4.15 (t, 2H), 4.25 (m, 1H), 6.70–6.85 (m, 3H) ppm.

EXAMPLE E2

The stirred mixture of 161.4 g D1. (crude), 1.61 l tetrahydrofuran and 0.474 l water is stirred at room temperature for 20 h with 0.474 l 2N LiOH. Then 1.61 l water is added and the tetrahydrofuran (1.7 l) evaporated off on a rotary evaporator. The resulting mixture is washed with tert-butyl methyl ether (0.5 l) and the aqueous solution of the intermediate E1 is obtained and immediately reacted further. While stirring, tert-butyl methyl ether (1.0 l) and 4N HCl (0.316 l) are added. The organic phase is separated off and stirred for 2 hours under reflux (with a water separator). The solution is cooled, dried over sodium sulfate and concentrated on a rotary evaporator. The crude title compound F1 obtained in this way (136.1 g) (content of title compound approx. 90%) is further reacted in example F4.

F) Preparation of Compounds of Formula IX

EXAMPLE F1

Preparation of

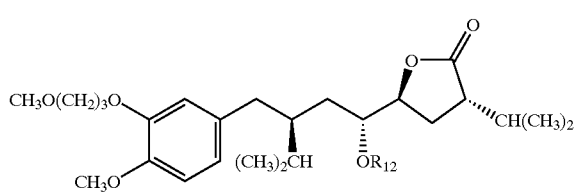

wherein R$_{12}$ is CH$_3$—SO$_2$—(G1).

To a solution of 0.325 g F1 and 8 ml dichloromethane, 0.156 ml triethylamine is added and the mixture cooled to 0° C. 0.087 ml methanesulfonyl chloride is added drop by drop and the mixture then stirred for 1 hour at room temperature. The reaction mixture is poured onto water (10 ml) and extracted with tert-butyl methyl ether (2×10 ml). The organic phases are washed consecutively with 5% aqueous sodium hydrogencarbonate solution (10 ml) and concentrated aqueous NaCl solution (10 ml). The combined organic phases are dried over sodium sulfate and concentrated by evaporation on a rotary evaporator. By means of flash chromatography (SiO$_2$ 60F/diethyl ether/hexane 2:1), title compound GC is obtained from the residue as a slightly yellowish oil (0.32 g, 82%) TLC R$_f$=0.18 (diethyl ether-hexane 2:1) $^1$H-NMR (300 MHz, CDCl$_3$): δ 0.85–1.05 (m, 12H), 1.55–2.25 (m, 9H), 2.40 (m, 1H), 2.60 (m, 1H), 2.75 (m, 1H), 2.95 (s, 3H), 3.40 (s, 3H), 3.60 (t, 2H), 3.85 (s, 3H), 4.15 (t, 2H), 4.45 (m, 1H), 4.80 (m, 1H), 6.70–6.85 (m, 3H) ppm.

EXAMPLE F2

Preparation of

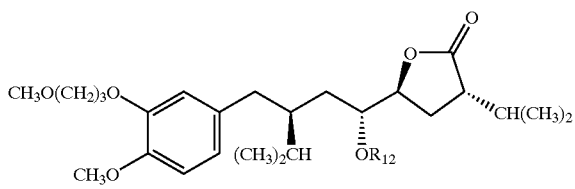

wherein R$_{12}$ is 4-BrC$_6$H$_5$—SO$_2$— (G2)

To a solution of 0.437 g F1 and 5 ml dichloromethane, 0.307 g 4-bromobenzenesulfochloride and 0.147 g 4-dimethylaminopyridine are consecutively added and the mixture then stirred for 24 hours at room temperature. The reaction mixture is poured onto iced water (30 ml) and extracted with diethyl ether (3×30 ml). The organic phases are washed consecutively with 5% aqueous sodium hydrogencarbonate solution (30 ml) and concentrated aqueous NaCl solution (30 ml). The combined organic phases are dried over sodium sulfate and concentrated by evaporation on a rotary evaporator. By means of flash chromatography (SiO$_2$ 60F/diethyl ether/hexane 1:1), title compound G2 is obtained from the residue as a slightly yellowish oil (0.304 g, 46%): TLC R$_f$=0.36 (diethyl ether-hexane 2:1).
$^1$H-NMR (300 MHz, CDCl$_3$): δ 0.80–1.0 (m, 12H), 1.55–2.20 (m, 9H), 2.25–2.45 (m, 2H), 2.70 (m, 1H), 3.40 (s, 3H), 3.60 (t, 2H), 3.90 (s, 3H), 4.15 (m, 2H), 4.35 (m, 1H), 4.65 (m, 1H), 6.60–6.85 (m, 3H), 7.60–7.75 (m, 4H) ppm.

EXAMPLE F3

Preparation of

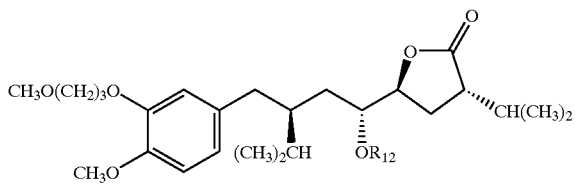

wherein R$_{12}$ is 4-CH$_3$C$_6$H$_5$—SO$_2$— (G3).

To a solution of 0.437 g F1 and 5 ml dichloromethane, 0.229 g 4-methylbenzenesulfochloride and 0.147 g 4-dimethylaminopyridine are added and the mixture then stirred for 24 hours at room temperature. The reaction mixture is poured onto iced water (30 ml) and extracted with diethyl ether (3×30 ml). The organic phases are washed consecutively with 5% aqueous sodium hydrogencarbonate solution (30 ml) and concentrated, aqueous NaCl solution (30 ml). The combined organic phases are dried over sodium sulfate and concentrated by evaporation on a rotary evaporator. By means of flash chromatography (SiO$_2$ 60F/diethyl ether/hexane 1:1), title compound G3 is obtained from the residue as a slightly yellowish oil (0.40 g, 68%) TLC R$_f$=0.26 (diethyl ether-hexane 2:1).
$^1$H-NMR (300 MHz, CDCl$_3$): (0.80–1.0 (m, 12H), 1.55–2.20 (m, 9H), 2.30–2.50 (m, 2H), 2.45 (s, 3H), 2.65 (m, 1H), 3.40 (s, 3H), 3.60 (t, 2H), 3.90 (s, 3H), 4.15 (m, 2H), 4.35 (m, 1H), 4.70 (m, 1H), 6.60–6.85 (m, 3H), 7.35 (d, 2H), 7.70 (d, 2H) ppm.

EXAMPLE F4

Preparation of G1

To a solution of 136.1 g F 1 (crude), prepared as described in example E2, and 0.86 l toluene, 52.8 ml triethylamine is added and the mixture cooled to 0° C. 29.45 ml methanesulfonyl chloride is added drop by drop and the mixture then stirred for 1 hour at 15° C. The reaction mixture is cooled to 0° C., 7.88 ml 3-dimethylamino-1-propylamine is added (the excess of methanesulfonylchloride is destroyed) and the mixture stirred for 15 minutes. The reaction mixture is washed with water (1 l), the organic phase separated off and the aqueous phase extracted again with toluene (0.6 l). The organic phases are washed consecutively with water/ saturated NaCl solution (5:1; 0.6 l) and saturated aqueous NaCl solution (0.6 l), dried over sodium sulfate and concentrated on a rotary evaporator. The crude title compound F1 obtained in this way (165 g) (content of title compound approx. 90%) is further reacted in example G2.

G) Preparation of Compounds of Formula II

EXAMPLE G1

Preparation of

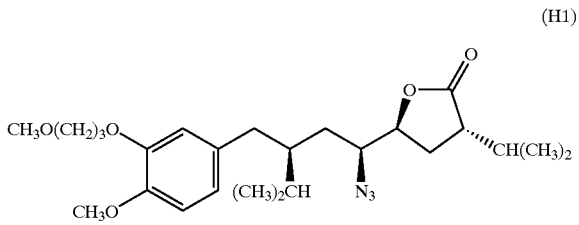

(H1)

A mixture of 9.5 g G1, 2.35 g sodium azide and 100 ml 1.3-dimethyl-3,4,5,6-tetrahydro-2(1H)-pyrimidone is stirred for 20 hours at 60° C. The reaction mixture is poured onto 500 ml water and extracted with tert-butyl methyl ether (3×200 ml). The organic phases are washed consecutively with water (3×500 ml), 5% aqueous sodium hydrogencarbonate solution (200 ml) and concentrated aqueous NaCl solution (200 ml). The combined organic phases are dried over sodium sulfate and concentrated on a rotary evaporator. By means of crystallization from 150 ml diisopropylether-hexane (1:2) at 0° C., title compound H1 is obtained from the residue as white crystals (5.62 g, 67%); m.p. 61–620 C; TLC R$_f$=0.41 (ethyl acetate-hexane 1:1); $^1$H-NMR (300 MHz, CDCl$_3$): δ 0.85–1.10 (m, 12H), 1.40 (m, 1H), 1.60–2.25 (m, 8H), 2.45 (m, 1H), 2.60 (m, 2H), 2,95 (m, 1H), 3,40 (s, 3H), 3.60 (t, 2H), 3.85 (s, 3H), 4.15 (t, 2H), 4.30 (m, 1H)), 6.70–6.85 (m, 3H) ppm.

Derivative H1 can be prepared by reaction of G2 or G3 by analogy with example G1.

EXAMPLE G2

Preparation of H1

A mixture of 165 g Gi (crude), 41.1 g sodium azide and 0.8 l 1.3-dimethyl-3,4,5,6-tetrahydro-2(1H)-pyrimidone is stirred for 20 hours at 60° C. The reaction mixture is cooled, poured onto 1.5 l water and extracted with methylcyclohexane (2×750 ml). The organic phases are washed consecutively with water (4×750 ml) and concentrated aqueous NaCl solution (750 ml). The combined organic phases are dried over sodium sulfate and concentrated to a volume of 900 ml on a rotary evaporator. The resulting solution is inoculated with 10 mg of title compound and stirred for 20 hours at ambient temperature. The resulting suspension is cooled to 0° C., and title compound H1 is obtained by filtration in the form of white crystals (104 g, 71%)

EXAMPLE G3

Preparation of H1

A mixture of 10.3 g G1 (crude), 50 ml methylcyclohexane, 40 ml 2N sodium azide (aqueous solution) and 0.4 g Aliquat® is stirred for 20 h at 80° C. The reaction mixture is cooled to 40° C., the aqueous phase is separated off and the organic phase washed at 40° C. with (2×40 ml). The organic phase is dried over sodium sulfate and filtered. The filtrate is inoculated with 5 mg of title compound and stirred for 20 hours at ambient temperature. The resulting suspension is cooled to 0° C., and title compound Hi is obtained by filtration in the form of white crystals (6.60 g, 71%).

H) Preparation of Compounds of Formula III

EXAMPLE H1

Preparation of

A mixture of 59.1 g H1, 41.82 g 3-amino-2,2-dimethyl-propionamide, 2.28 g 2-hydroxypyridine in 59.1 ml triethylamine is stirred over a period of 16 hours at 90° C. Then 33 ml triethylamine is distilled off over a period of 0.5 hours, and the residue is agitated for a further 8.5 hours at 90° C. The cooled reaction mixture is extracted between ethyl acetate (3×500 ml), saturated aqueous sodium hydrogencarbonate solution (1×500 ml) and saturated sodium chloride solution (1×500 ml). The combined organic phases are dried with 100 g sodium sulfate, filtered and concentrated on the rotary evaporator. The residue is dried and crude title compound F1 is obtained as an oil (78.4 g, quantitative) (HPLC assay: 88.5%): TLC $R_f$=0.13 (ethyl acetate-hexane 4:1); chromatographed sample: TLC $R_f$=0.13 (ethyl acetate/hexane 4:1); $^1$H-NMR (500 MHz, CDCl$_3$, δ): 0.85–0.96 (m, 12H), 1.23 (s, 6H), 1.30–1.40 (m, 1H), 1.53–1.80 (m, 5H), 1.82–1.93 (m, 1H), 2.06–2.14 (m, 3H), 2.45–2.57 (m, 2H), 2.87–2.92 (m, 1H), 3.13 (d, 1H), 3.32–3.52 (m, 3H), 3.36 (s, 3H), 3.59 (t, 2H), 3.84 (s, 3H), 4.12 (t, 2H), 5.51 (bs, 1H), 6.01 (bs, 1H), 6.43 (t, 1H), 6.72 (dd, 1H), 6.75 (d, 1H), 6.81 (d, 1H) ppm.

EXAMPLE H2

Preparation of J1

A mixture of 9.23 q H1, 6.97 g 3-amino-2,2-dimethylpropionamide, 1.90 g 2-hydroxypyridine and 5.0 ml triethylamine is stirred over a period of 24 hours at 65° C. The cooled reaction mixture is extracted between tert-butyl methyl ether (2×150 ml) and water (2×150 ml). The combined organic phases are dried over sodium sulfate, filtered and concentrated on a rotary evaporator. The residue is dried and crude title compound Fl is obtained as an oil (11.65 g, quantitative) (HPLC assay: >95%).

EXAMPLE H3

Preparation of J1

A mixture of 4.62 g H1, 3.48 g 3-amino-2,2-dimethylpropionamide and 0.95 g 2-hydroxypyridine is stirred over a period of 24 hours at 65° C. The cooled reaction mixture is extracted between tert-butyl methyl ether (2×100 ml) and water (2×100 ml). The combined organic phases are dried over sodium sulfate, filtered and concentrated on a rotary evaporator. The residue is dried and crude title compound J1 is obtained as an oil (5.75 g, quantitative) (HPLC assay: >95%).

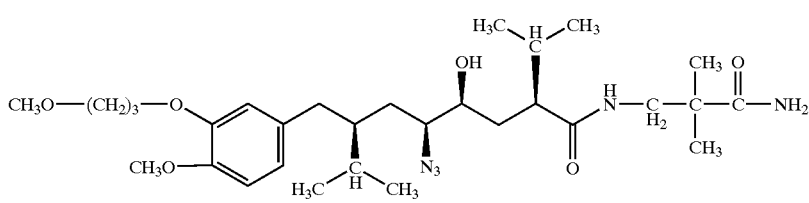

(J1)

J) Hydrogenation of the Azide Group to Form Compounds of Formula I

EXAMPLE J1

Preparation of

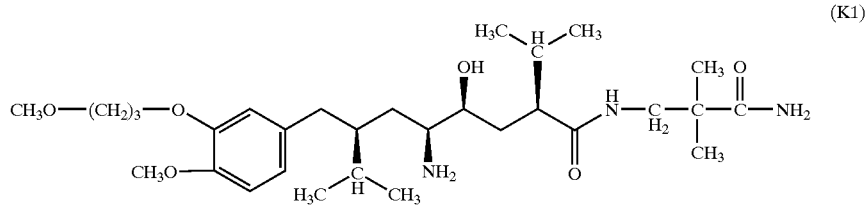

(K1)

78.4 g (HPLC assay: 88.5%) J1 (crude) is hydrogenated for 3 hours in the presence of 3.92 g Pd/C 5% and 7.2 ml ethanolamine in 700 ml tert-butyl methyl ether at ambient temperature and 3.0 bar. The reaction mixture is filtered and the catalyst washed with 300 ml tert-butyl methyl ether. The filtrate is washed consecutively with 400 ml 2N NaOH and 400 ml brine. The aqueous phases are then extracted with tert-butyl methyl ether (2×400 ml). The combined organic phases are dried with 100 g sodium sulfate and concentrated by evaporation. The residue is mixed with 7.31 g fumaric acid and dissolved in 200 ml ethanol and filtered until clear. The filtrate is concentrated by evaporation to a total weight of 104 g and dissolved in 1.7 l acetonitrile at 35° C. The resulting solution is inoculated with 10 mg of title compound (hemifumarate) and stirred for 17 hours at ambient temperature. The suspension is cooled to 0° C. and filtered off by suction after 2 hours. The residue is washed with acetonitrile (3×200 ml) and then dried in a vacuum at 35° C. The title compound K1 (hemifumarate) is obtained as white crystals (59.5 g, 81% in relation to J1): 1H NMR (360 MHz, DMSO-$d_6$); δ 0.7–0.9 (m, 12H), 1.04 (s, 6H), 1.27 (m, 3H), 1.4–1.8 (m, 4H), 1.94 (m, 2H), 2.23 (m, 1H), 2.35 (dd, J 8.4, 8.0 Hz, 1H), 2.45 (m, 1H), 3.08 (m, 2H), 3.2–3.5 (m, 2H), 3.24 (s, 3H), 3.47 (t, J=6.4 Hz, 2H), 3.74 (s, 3H), 3.97 (t, J=6.4 Hz, 2H), 6.37 (s, 1H), 6.68 (dd, J=8.0, 2.0 Hz, 1H), 6.77 (d, J=6 Hz, 1H), 6.80 (bs, 1H), 6.83 (d, J=8 Hz, 1H), 7.13 (bs, 1H), 7.49 (t, J=6 Hz, 1H).

What is claimed is:

1. Process for preparation of compounds of formula I,

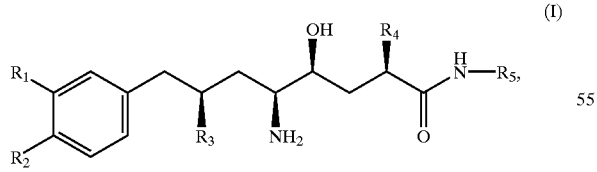

(I)

wherein $R_1$ and $R_2$ are, independently of one another, H, $C_1$–$C_6$alkyl, $C_1$–$C_6$halogenalkyl, $C_1$–$C_6$alkoxy, $C_1$–$C_6$alkoxy-$C_1$–$C_6$alkyl, or $C_1$–$C_6$alkoxy-$C_1$–$C_6$alkyloxy, $R_3$ is $C_1$–$C_6$alkyl, $R_4$ is $C_1$–$C_6$alkyl, and $R_5$ is $C_1$–$C_6$alkyl, $C_1$–$C_6$hydroxyalkyl, $C_1$–$C_6$alkoxy-$C_1$–$C_6$-alkyl, $C_1$–$C_6$alkanoyloxy-$C_1$–$C_6$alkyl, $C_1$–$C_6$aminoalkyl, $C_1$–$C_6$alkylamino-$C_1$–$C_6$alkyl, $C_1$–$C_6$-dialkylamino-$C_1$–$C_6$-alkyl, alkanoylamido-$C_1$–$C_6$-alkyl, HO(O)C—$C_1$–$C_6$-alkyl, $C_1$–$C_6$alkyl-O—(O)C—$C_1$–$C_6$alkyl, $H_2N$—C(O)—$C_1$–$C_6$alkyl, $C_1$–$C_6$alkyl-HN—C(C)—$C_1$–$C_6$alkyl or ($C_1$–$C_6$alkyl)$_2$N—C(O)—$C_1$–$C_6$-alkyl, a) by reacting a compound of formula II,

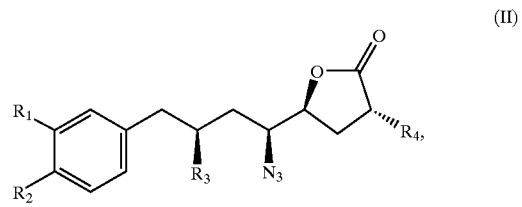

(II)

with an amine of formula $R_5$—$NH_2$ to form a compound of formula III,

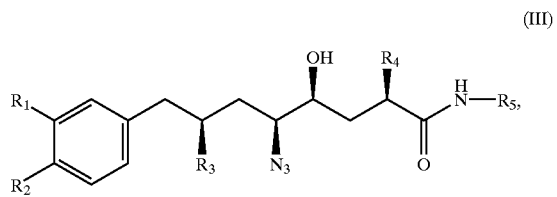

(III)

and b) by reducing the azide group of the compound of formula III to the amine group and isolating the compounds of formula I, if necessary with the addition of a salt-forming acid, comprising the preparation of compounds of formula II by c1) reacting a compound of formula IV,

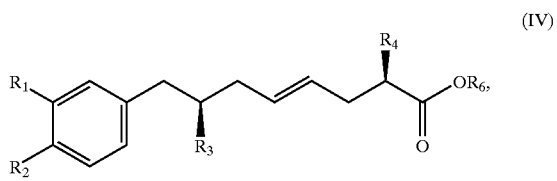

(IV)

wherein $R_6$ is $C_1$–$C_{20}$alkyl, $C_3$–$C_{12}$cycloalkyl, $C_3$–$C_{12}$cycloalkyl-$C_1$–$C_6$alkyl, $C_6$–$C_{10}$aryl or $C_6$–$C_{10}$-aryl-$C_1$–$C_6$alkyl, with a halogenation agent to form a compound of formula VI, or c2) reacting a carboxylic acid of formula V, or a salt of this carboxylic acid,

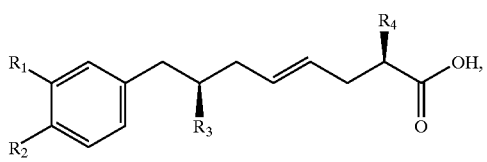
(V)

with a halogenation agent to form a compound of formula VI,

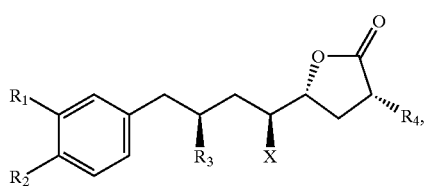
(VI)

wherein X is Cl, Br or I, d) reacting the compound of formula VI in the presence of an alkali metal or alkaline earth metal hydroxide or an alcohol to form a compound of formula VII,

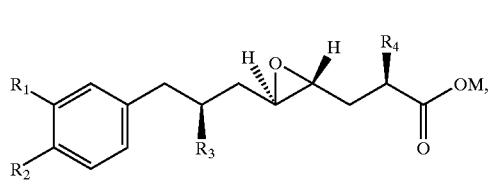
(VII)

wherein M is an alkali metal, an equivalent alkaline earth metal or the residue of an alcohol minus a hydroxyl group, e) hydrolysing the compound of formula VII in the presence of an acid to form a compound of formula VIII,

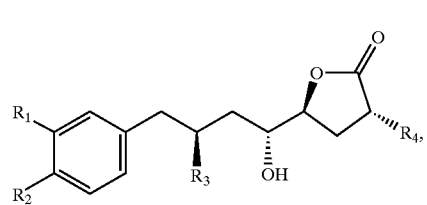
(VIII)

f) substituting the hydrogen atom of the hydroxyl group in the compound of formula VIII and converting it to a leaving group AO to form compounds of formula IX,

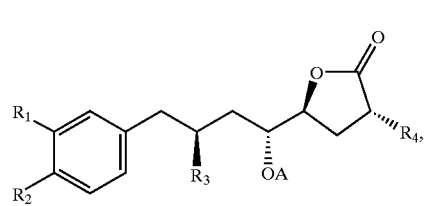
(IX)

g) and then reacting the compound of formula IX with an azidation agent to form a compound of formula II, or h) reacting the compound of formula VIII directly with a zinc azide/-bis-pyridine complex in the presence of a tertiary phosphine and an azodicarboxylate, if necessary in an organic solvent, to form a compound of formula II.

2. A process according to claim 1 comprising an embodiment wherein $R_1$ is $C_1$–$C_4$alkoxy or $C_1$–$C_4$alkoxy-$C_1$–$C_4$alkyloxy, $R_2$ is $C_1$–$C_4$alkoxy, $R_3$ is $C_1$–$C_4$alkyl, $R_4$ is $C_1$–$C_4$alkyl and $R_5$ is $H_2NC(O)$—$C_1$–$C_6$alkyl which if necessary is N-monosubstituted or N-di-$C_1$–$C_4$alkyl substituted.

3. A process according to claim 2 comprising an embodiment wherein $R_1$ is 1-methoxyprop-3-yloxy and $R_2$ is methoxy.

4. A process according to claim 2 comprising an embodiment wherein $R_3$ and $R_4$ are in each case isopropyl.

5. A process according to claim 2 comprising an embodiment wherein $R_5$ is $H_2NC(O)$—$C_1$–$C_6$alkyl.

6. A process according to claim 1 comprising an embodiment wherein $R_1$ is methoxy-$C_2$–$C_4$alkyloxy, $R_2$ is methoxy or ethoxy, $R_3$ is $C_2$–$C_4$alkyl, $R_4$ is $C_2$–$C_4$alkyl and $R_5$ is $H_2NC(O)$—$C_1$–$C_6$alkyl.

7. A process according to claim 1 comprising an embodiment wherein $R_1$ is 3-methoxy-prop-3-yloxy, $R_2$ is methoxy, $R_3$ and $R_4$ are each 1-methyleth-1-yl, and $R_5$ is $H_2NC(O)$—$[C(CH_3)_2]$—$CH_2$—.

8. Compounds of formula X,

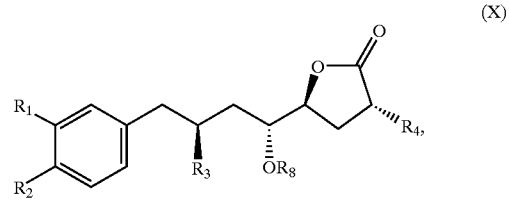
(X)

wherein $R_1$ and $R_2$ are, independently of one another, H, $C_1$–$C_6$alkyl, $C_1$–$C_6$halogenalkyl, $C_1$–$C_6$alkoxy, $C_1$–$C_6$alkoxy-$C_1$–$C_6$alkyl, or $C_1$–$C_6$alkoxy-$C_1$–$C_6$alkyloxy, $R_3$ is $C_1$–$C_6$alkyl, $R_4$ is $C_1$–$C_6$alkyl, and $R_8$ is hydrogen or $R_8O$ is a leaving group.

9. Compounds of formula VII,

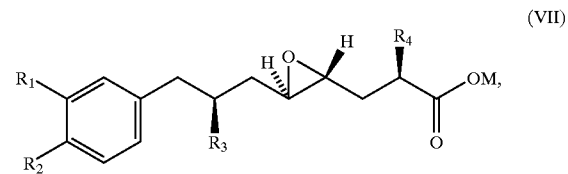
(VII)

wherein M is an alkali metal, an equivalent alkaline earth metal or the residue of an alcohol minus a hydroxyl group, and $R_1$ and $R_2$ are, independently of one another, H, $C_1$–$C_6$alkyl, $C_1$–$C_6$halogenalkyl, $C_1$–$C_6$alkoxy, $C_1$–$C_6$alkoxy-$C_1$–$C_6$alkyl, or $C_1$–$C_6$alkoxy-$C_1$–$C_6$alkyloxy, $R_3$ is $C_1$–$C_6$alkyl, and $R_4$ is $C_1$–$C_6$alkyl.

10. Compounds of formula XIII,
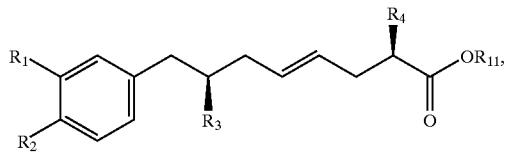
(XIII)
wherein $R_{11}$ is an alkali metal, an equivalent alkaline earth metal, hydrogen or the residue of an alcohol minus a hydroxyl group, and
$R_1$ and $R_2$ are, independently of one another, H, $C_1$–$C_6$alkyl, $C_1$–$C_6$halogenalkyl, $C_1$–$C_6$alkoxy, $C_1$–$C_6$alkoxy-$C_1$–$C_6$alkyl, or $C_1$–$C_6$alkoxy-$C_1$–$C_6$alkyloxy, $R_3$ is $C_1$–$C_6$alkyl, and $R_4$ is $C_1$–$C_6$alkyl.
* * * * *